(12) United States Patent
Eschenbacher

(10) Patent No.: US 10,786,179 B2
(45) Date of Patent: Sep. 29, 2020

(54) BREATHING GAS MEASURING DEVICE

(71) Applicant: CareFusion Germany 234 GmbH, Höchberg (DE)

(72) Inventor: Hermann Eschenbacher, Reichenberg (DE)

(73) Assignee: VYAIRE MEDICAL GMBH, Höchberg (DE)

( * ) Notice: Subject to any disclaimer, the term of this patent is extended or adjusted under 35 U.S.C. 154(b) by 701 days.

(21) Appl. No.: 14/704,157

(22) Filed: May 5, 2015

(65) Prior Publication Data

US 2016/0045138 A1 Feb. 18, 2016

(30) Foreign Application Priority Data

Aug. 13, 2014 (DE) .................. 10 2014 111 528

(51) Int. Cl.
| | |
|---|---|
| *A61B 5/097* | (2006.01) |
| *A61B 5/083* | (2006.01) |
| *A61B 5/08* | (2006.01) |
| *A61M 16/08* | (2006.01) |
| *A61M 16/00* | (2006.01) |
| *A61M 16/20* | (2006.01) |

(Continued)

(52) U.S. Cl.
CPC .............. *A61B 5/097* (2013.01); *A61B 5/082* (2013.01); *A61B 5/083* (2013.01); *A61M 16/0066* (2013.01); *A61M 16/085* (2014.02); *A61M 16/20* (2013.01); *A62B 17/04* (2013.01); *A61B 5/087* (2013.01); *A61B 2560/0443* (2013.01); *A61M 2205/11* (2013.01)

(58) Field of Classification Search
CPC ............ A61B 5/087; A61B 5/097; A61B 5/08
See application file for complete search history.

(56) References Cited

U.S. PATENT DOCUMENTS

| 4,106,504 A | * | 8/1978 | York ..................... B63C 11/325 |
|---|---|---|---|
| | | | 128/204.24 |
| 4,832,042 A | * | 5/1989 | Poppendiek .......... A61B 5/097 |
| | | | 128/205.19 |

(Continued)

FOREIGN PATENT DOCUMENTS

JP 2013144104 A 7/2013

OTHER PUBLICATIONS

Extended European Search Report for Application No. 1566454.7, dated Oct. 19, 2015, 7 pages.

(Continued)

*Primary Examiner* — Christian Jang
*Assistant Examiner* — Karen E Toth
(74) *Attorney, Agent, or Firm* — Morgan, Lewis & Bockius LLP

(57) ABSTRACT

A respiratory air measuring device is provided through which a measuring air stream flows for measuring at least one component of the respiratory air of a patient. The respiratory air measuring device includes a sensor device and a flow generator disposed downstream for generating a measuring air stream. A flow nozzle is disposed in a channel portion to affect flow, wherein a generator air stream coming from the flow nozzle creates the measuring air stream. The respiratory air measuring device may be partially disassembled for effective cleaning.

20 Claims, 2 Drawing Sheets

(51) Int. Cl.
A62B 17/04 (2006.01)
A61B 5/087 (2006.01)

(56) References Cited

U.S. PATENT DOCUMENTS

| | | | | |
|---|---|---|---|---|
| 5,081,871 | A * | 1/1992 | Glaser | A61B 5/083 |
| | | | | 422/84 |
| 5,495,744 | A * | 3/1996 | Ueda | A61B 5/083 |
| | | | | 422/84 |
| 6,076,392 | A * | 6/2000 | Drzewiecki | A61M 16/0051 |
| | | | | 422/83 |
| 2001/0029340 | A1 * | 10/2001 | Mault | A61M 16/08 |
| | | | | 600/532 |
| 2007/0232950 | A1 * | 10/2007 | West | A61B 5/083 |
| | | | | 600/532 |
| 2009/0156952 | A1 | 6/2009 | Hunter et al. | |
| 2009/0326396 | A1 | 12/2009 | Aliverti et al. | |
| 2012/0277617 | A1 | 11/2012 | Eichler | |
| 2012/0294876 | A1 | 11/2012 | Zimmerman | |
| 2015/0025407 | A1 * | 1/2015 | Eichler | A61B 5/087 |
| | | | | 600/532 |
| 2015/0059749 | A1 * | 3/2015 | Nitta | A61M 16/0051 |
| | | | | 128/204.18 |

OTHER PUBLICATIONS

International Search Report and Written Opinion for Application No. PCT/EP2015/059881, dated Oct. 6, 2015, 10 pages.
European Office Action for Application No. 15166454.7, dated Aug. 1, 2017, 3 pages.

* cited by examiner

BREATHING GAS MEASURING DEVICE

CROSS-REFERENCE TO RELATED APPLICATION

This application claims priority to German Application No. 102014111528.7 filed on Aug. 13, 2014, entitled "BREATH MEASUREMENT DEVICE, which issued on Apr. 12, 2016, as German Patent No. 102014111528B3, the entire contents of which is incorporated by reference herein.

BACKGROUND OF THE INVENTION

The present disclosure relates to a respiratory air measuring device for measuring at least one component in the respiratory air of a patient.

In many medical treatment settings, respiratory air measuring devices are frequently used for measurement in patients suffering from metabolic disorders and, in contrast, are not used if the patient has an infection. However, the possibility cannot be ruled out that individual patients secrete germs with the respiratory air, which are then guided through the respiratory air measuring device and can adhere to the respiratory air measuring device. It is desirable to provide a respiratory air measuring device with improved cleanability.

SUMMARY

Some disclosed embodiments provide a respiratory air measuring device including an inlet opening and an outlet opening, wherein a measuring air stream is configured to flow from the inlet opening to the outlet opening. The device also includes a connector disposed on the inlet opening, the connector configured to fasten the respiratory air measuring device directly or indirectly to a connecting opening of a covering hood. The device may further include at least one sensor device disposed downstream of the connecting opening in a flow direction of the measuring air stream, the sensor device configured to measure at least one component of the respiratory air of a patient. The device may also include a flow generator disposed downstream of the sensor device in the flow direction of the measuring air stream, the flow generator configured to generate the measuring air stream in a channel portion that is open to the inlet opening and to the outlet opening. The flow generator includes an air connection configured to supply a generator air stream and at least one flow nozzle from which the generator air stream is configured to exit, the flow nozzle configured to affect the generator air stream flow so that the generator air stream creates the measuring air stream.

Some disclosed embodiments also provide a respiratory air measuring device including a housing having an inlet opening, an outlet opening, and a channel portion disposed between the inlet portion and the outlet portion, wherein a measuring air stream is configured to flow from the inlet opening to the outlet opening. The device also includes a connector configured to fasten the inlet opening to a respiratory hood and at least one sensor device configured to measure at least one component of respiratory air of a patient. The device can further include a flow generator configured to generate the measuring air stream in the channel portion, the flow generator. The flow generator includes an air connection configured to supply a generator air stream from a generator and a flow nozzle configured to direct the generator air stream to create the measuring air stream.

Some disclosed embodiments provide a method of measuring respiratory air including connecting an inlet opening of a respiratory air measuring device to a respiratory hood and connecting a flow generator to a channel portion of the respiratory air measuring device, the channel portion including a flow nozzle oriented in a predetermined position. The method may include generating, by the flow generator, a generator air stream to create a measuring air flow in the respiratory air measuring device. The method may further include measuring, by at least one sensor, at least one component of respiratory air of a patient positioned within the respiratory hood, the measuring air flow flowing from the inlet opening, past the at least one sensor and out an outlet opening.

BRIEF DESCRIPTION OF THE DRAWINGS

In the following, embodiments of the apparatus and methods according to the disclosure are described, making reference to the attached drawings, in which.

DETAILED DESCRIPTION OF THE PREFERRED EMBODIMENTS

Figure 1:
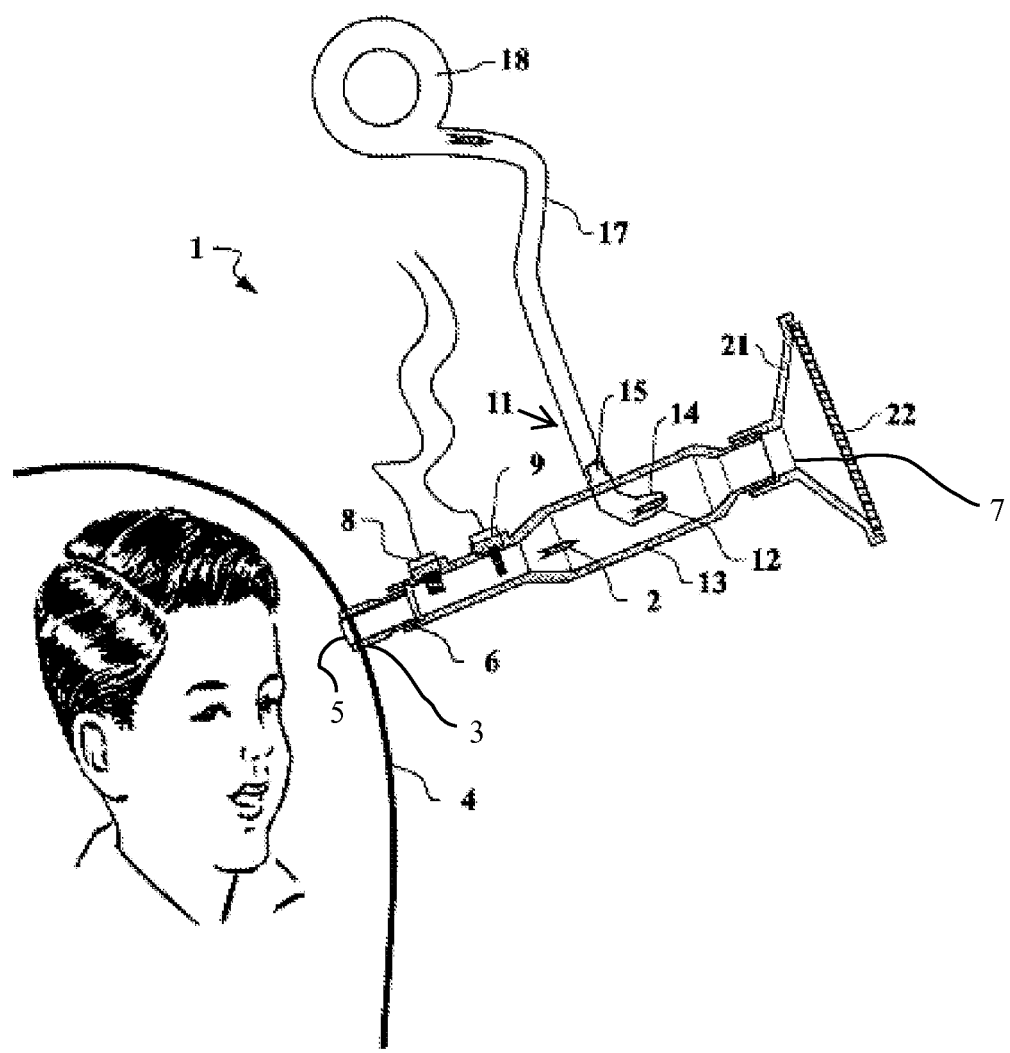
FIG. 1 is a cross-sectional perspective view of an embodiment of a respiratory air measuring device.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Some respiratory air measuring devices capture the respiratory air directly via a mouthpiece and guides it past a respiratory air sensor for detecting the respiratory air. In order to ensure the necessary volumetric flow with simultaneous reduction of the breathing resistance, a suction pump is provided downstream of the respiratory air sensor. Also, a constant volumetric flow of a breathable gas can be supplied to the device. During inhalation, the breathable gas can be guided to the patient via branching air channels, whereas during exhalation the supplied breathable gas escapes with the exhaled air via a side channel.

In some respiratory air measuring devices, a variation in the measurement of the breathing resistance can be achieved in that an air flow superimposed on the respiratory air is generated by a pump. Here, for measuring the breathing resistance, it may be desirable for the measuring device to have a mouthpiece, so that the breathing pressure can be correctly detected.

Although measurement by means of a respiratory air measuring device having a mouthpiece can supply accurate results, the use of such a system over a relatively long time period generally proves to be uncomfortable may not be acceptable to many patients.

Therefore, consideration is given to those respiratory air measuring devices that can be attached to a hood or the like, wherein the hood can be arranged over a patient's head so that the patient can breathe freely under the hood.

For example, in some respiratory air measuring devices, a sensor device in the form of a perforated plastic tube with an integrated $CO_2$ sensor is disposed inside a hood. Respiration is determined by a pressure sensor, so that during an exhalation phase condensed water and respiratory air from the prior measurement can be drawn off out of the sensor arrangement. In this solution, however, for determination of the respiratory air it is necessary that the hood for the most part rests tightly on the patient's face, since otherwise the proportion of extraneous air is uncertain and thus the determined measured value is not reliable.

Since, in many cases, an absolute seal cannot be produced and also the necessary actions for measurement of the respiratory air are disproportionate, the respiratory air to be measured is actively drawn in through an inlet of the respiratory air measuring device and after measurement is expelled through an outlet into the environment. Accordingly, some respiratory air measuring devices form a flow channel in which both a sensor for measuring the component of the respiratory air and also a fan for generating the necessary air flow are disposed. For flexible handling of the respiratory air measuring device and the hood, the respiratory air measuring device is generally constructed separately from the hood, so that the device can be coupled to the hood. The embodiment of the hood is irrelevant for the present disclosure.

The embodiments described herein provide respiratory air measuring devices that serve for measuring at least one component in the respiratory air of a patient. In many cases the oxygen and/or carbon dioxide content may be determined, though the type of measurement is irrelevant for the present disclosure. For the measurement, a measuring air stream flows through the housing of the respiratory air measuring device from an inlet opening to an outlet opening. Although it would be conceivable to use the respiratory air measuring device autonomously, it is preferred that the respiratory air measuring device be disposed on a covering or respiratory hood, allowing the patient's respiratory air to be fed in a controlled manner to the respiratory air measuring device. For example, the respiratory air measuring device may have a connector disposed at the inlet opening so that the respiratory air measuring device may be directly or indirectly fastened to a connecting opening of a covering hood.

The respiratory air measuring device may further include at least one sensor device for measuring the respiratory air. Downstream of the sensor device, a flow generator may generate a measuring air stream. The flow generator may be located of disposed before the outlet opening. Further, between the sensor device and the outlet opening the flow generator may have a channel portion that is open to both sides and in which the measuring air stream may be generated by the flow generator.

Accordingly, the cleanability of the respiratory air measuring device may be improved by replacing the customary fan with an embodiment of the disclosed flow generator. The flow generator may have an air connection through which a generator air stream may be guided. At least one flow nozzle from which the generator air stream may escape at high speed is located within the channel portion. The channel portion may be configured for affecting air flow so that the generator air stream coming from the flow nozzle creates the measuring air stream. For example, consideration should be given not only to the geometry of the channel portion but also to the geometry and orientation of the flow nozzle inside the channel portion to achieve the desired flow mechanics.

A significantly improved cleanability of the respiratory air measuring device may be achieved by the preferred embodiment of the respiratory air measuring device with a flow generator that employs a generator air stream for generating the measuring air stream. For example, there is no fan driven by an electric motor having movable or particularly delicate parts within the flow generator. Instead there is only a flow nozzle that may be readily cleaned, disinfected or sterilized (e.g., by flushing).

In a disclosed embodiment, the respiratory air measuring device may be attached directly to the covering hood. Accordingly, the connector may be designed to be complementary to the connecting opening on the covering hood.

In a disclosed embodiment, the connector may be connected to a hose portion having a hose connection on the end remote from the connector. Accordingly, the hose connection may be designed to be complementary to the connecting opening. For example, the connecting opening as well as the connector may be in the form of a cylindrical pipe stub on which the hose portion is fitted and fixed by its two ends.

In order to ensure sealing with simple handling, the connection between the connector and the connecting opening, or between the hose connection and the connecting opening, may be configured as a bayonet connection.

The hose portion may be fixed securely on the connector. However, for cleaning it is preferable to provide for releasability between the connector and the hose portion. Here, not only the hose connection may be fastened to the connecting opening, but also, with the hose portion omitted, the connector may be fastened directly to the connecting opening. In this respect the hose portion forms an extension hose.

Both with regard to the effectiveness of the flow generator and to the convenient use of the respiratory air measuring device, in particular observing the noise level to be expected, it is preferred that a generator air stream is delivered with an overpressure of up to 1.5 bars, i.e. is correspondingly present at the air connection. An overpressure of up to 0.5 bar using a greater air stream is preferred to minimize the likelihood of noise being generated.

Various embodiments are provided with regard to the type of delivery of the generator air stream. In an embodiment, an external compressed air supply may be a prerequisite for use of the respiratory air measuring device. Accordingly, the respiratory air measuring device may be connected to the compressed air supply so that compressed air can be delivered. Here, in order to regulate the required generator air stream it may be necessary for a compressed air valve to be disposed directly or indirectly before the air connection through which the compressed air is delivered. The compressed air valve may be a non-adjustable element that allows the passage of a constant volumetric air flow, or the compressed air valve may be an adjustable element that allows for a variable volumetric air flow.

Alternatively, instead of a direct or indirect connection to an external compressed air supply to the air connection, an adjustable blower or an adjustable fan may be provided.

A blower or a fan can be used to provide that the sufficient generator air stream is available. The use of the blower or fan may render the external compressed air supply superfluous. Furthermore, with appropriate selection of the blower or the fan a generator air stream with advantageous pressure may already be available without the need for a compressed air valve, although a compressed air valve may still be used.

Furthermore, the compressed air valve or the blower or fan may be adjustable in stages or continuously, so that an adaptation to the respective particularly advantageous pressure and/or the particularly advantageous velocity of the generator air stream takes place. Thus the generator air stream used in each case may be influenced flexibly, so that the measuring air stream can be influenced as desired.

With regard to the flow generator, the choice of the nozzle in relation to the channel cross-section of the channel portion and taking into account the generator air stream to be generated, the flow nozzle may be configured to have an opening cross-section between 5 $mm^2$ and 100 $mm^2$. For example, cross-sections in the range between 10 $mm^2$ and 50 $mm^2$ may be particularly advantageous. Here, the measuring air stream, which is generally necessary in a range between 10 l/min to 100 l/min, should be taken into account. Taking into account an advantageous effectiveness of the flow generator and also taking into account the lowest possible noise level due to the flow generator, a generator air stream of a desired order of magnitude (e.g., 50% of the measuring air stream) may be generated. As a result, the channel cross-section to be used may have a free cross-section between 100 $mm^2$ and 600 $mm^2$, and in particular, between 200 $mm^2$ and 400 $mm^2$.

Various embodiments may be provided with regard to the positioning and the choice of the number of flow nozzles. On the one hand, a plurality of flow nozzles may be distributed in the channel portion. However, this may impact the cleanability of the flow generator. Therefore, from the point of view of cleanability, it is preferred that a flow nozzle be located in the interior of the channel portion and the measuring air stream may circulate mostly or completely around the flow nozzle. For example, a round flow nozzle may be positioned centrally in a round channel portion having around channel cross-section, allowing the measuring air stream to flow around the complete circumference of the flow nozzle.

In some embodiments, instead of a flow nozzle positioned inside the channel portion, an annular gap on the periphery of the channel portion may be used as a flow nozzle. Here, the generator air stream coming out of the flow nozzle circulates around the measuring air stream, which is thus guided centrally through the channel portion with the flow nozzle. For example, the channel portion may be configured with a Coanda profiled section, which may provide a particularly effective generation of a measuring air stream when the generator air stream is introduced.

With regard to cleanability, consideration should be given to the extent to which the sensor device is accessible for the intended cleaning process. Therefore, because of electronic elements which are customarily inside a conventional sensor device, it is preferable if at least the components of the sensor device which are not in contact with the measuring air stream are removable. Thus, special protection for the sensor device may be omitted when cleaning in hot water, for example. Also, the part of the respiratory air measuring device potentially contaminated with germs from the respiratory air loads may be cleaned advantageously using various cleaning processes. Alternatively, for cleaning of the respiratory air measuring device the sensor device may be removed completely therefrom, wherein the part of the sensor device in contact with the measuring air stream may then be cleaned separately.

Furthermore, as an alternative or in addition to the regular cleaning of the parts of the sensor device in contact with the measuring air stream, the component of the sensor device in contact with the measuring air stream may be replaceable as a consumable item at regular intervals or as required after every measurement. Thus, a particularly reliable measurement of the respiratory air is made possible since the sensor device in each case supplies an error-free measurement result without contamination. Further, germs which may not be removable from the components of the sensor device in contact with the measuring air stream do not lead to complications.

For control of the respiratory air measuring device, in particular the flow generator, and for the most precise evaluation possible of the data determined by the sensor device, a volumetric flow measuring device may be disposed between the inlet opening and the flow generator for measurement of the volumetric flow of the measuring air stream. Regardless of the type of volumetric flow measuring device, the magnitude of the measuring air stream may be ascertained so that in the event of deviation from the required desired value the generator air stream may be influenced and the data obtained from the sensor device may be evaluated correctly for measurement of the respiratory air.

With regard to the cleanability of the respiratory air measuring device, for removal of the volumetric flow measuring device in parts or as a whole, the same procedure applies as in the case of the sensor device for measurement of the respiratory air.

With regard to the noise level, a convenient use of the respiratory air measuring device may be achieved by a sound absorber for reduction of the sound produced (e.g., in the flow generator) disposed downstream of the flow generator in the flow direction.

In order to prevent a possible undesirable air flow out of the outlet opening, a diffuser may be used for widening the exiting air stream so that the exiting air stream is barely perceptible and thus does not appear negative.

Further, an air filter element may be used, in particular at the outlet end. The filter element, may retain particles carried along with the measuring air stream during the measuring operation and may prevent contamination of the respiratory air measuring device (e.g., dust) while the respiratory air measuring device is not in use.

With further regard to the cleanability of the respiratory air measuring device, the respiratory air measuring device may be configured to be disinfected. For example, the removable components of the respiratory air measuring device which are not in contact with the measuring air stream may be removed beforehand, so that they do not have to be subjected to the disinfection process. Also, the respiratory air measuring device may also be sterilizable, so that no concerns remain about the use of the respiratory air measuring device even in patients with infectious diseases.

The channel-like structure of the respiratory air measuring device at least makes mechanical cleaning of the interior difficult. Therefore, in view of both cleaning and disinfection/sterilization, the respiratory air measuring device may be configured to be dismantled into individual portions along the length of the device. For example, a bayonet connection may be used for attachment of the removable components of the sensor device, the volumetric flow measuring device and/or the air hose.

It does not show an embodiment in which the respiratory air measuring device is connected by means of a hose portion to the covering hood, which can be easily achieved in the illustrated example using for example a suitable extension hose as a hose portion.

In FIG. 1, a respiratory air measuring device 1 is shown positioned directly on a covering hood 4 of a respiratory patient. The covering hood 4 covers a patient whose respiratory air is to be measured. The covering hood 4 has a connecting opening 3 to which the respiratory air measuring device 1 is fastened by a connector 6 disposed at an inlet opening 5. In this case, a measuring air stream 2 flows through the respiratory air measuring device 1 from the inlet opening 5 to an outlet opening 7, wherein a sensor device 8 for measuring at least one component of the patient's respiratory air is attached in an inlet region. A volumetric flow measuring device 9 for determining the flow rate or the volumetric flow of the measuring air stream 2 flowing through the respiratory air measuring device 1 is located or disposed downstream of the sensor device 8.

The measuring air stream 2 is generated from a flow generator 11 by blowing a generator air stream 12 from a flow nozzle 14 into the respiratory air measuring device 1. The flow nozzle 14 is positioned centrally in a channel portion 13 of the respiratory air measuring device 1. Thus, because of a higher exit velocity of the generator air stream 12, the surrounding measuring air stream 2 is entrained. The generator air stream 12 is delivered by connection of a compressed air hose 17 to an air connection 15 of the flow generator 11, wherein a blower 18 for generating the generator air stream 12 adjoins the compressed air hose 17. Further, the respiratory air measuring device 1 has a diffuser 21 and an air filter element 22 disposed downstream of the flow generator 11.

Figure 2:
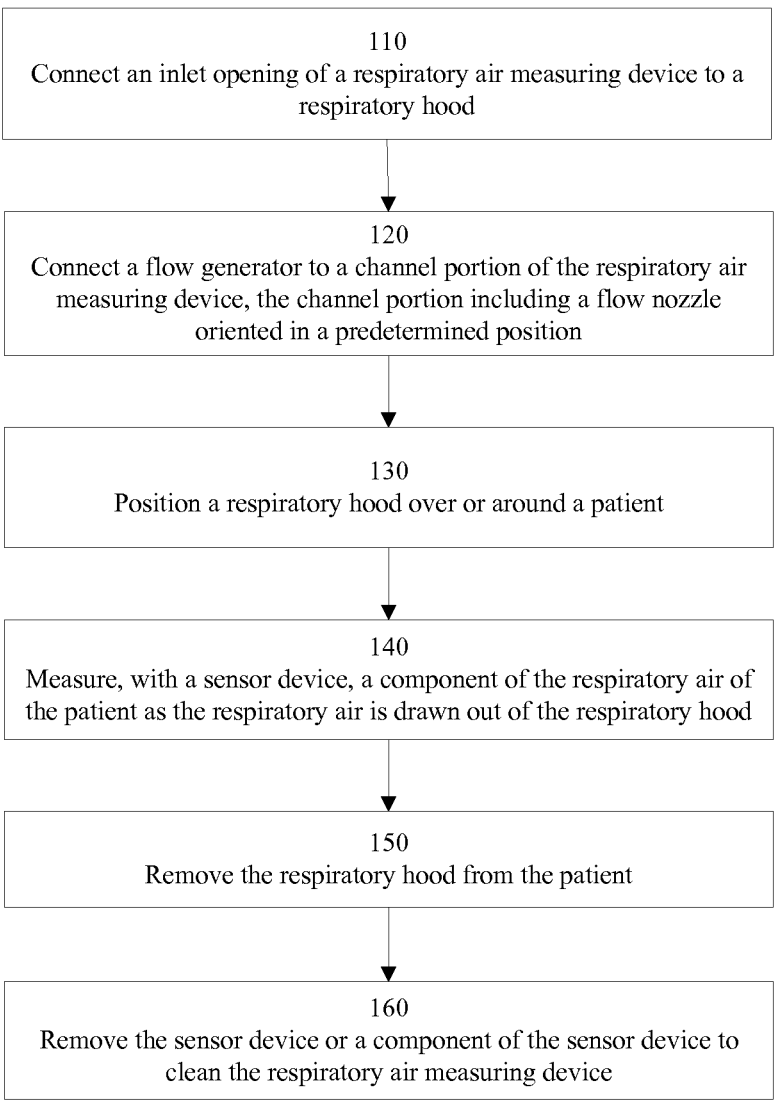
FIG. 2 is a flow chart illustrating steps in a method for using and cleaning a respiratory air measuring device, according to some embodiments.

Methods consistent with the present disclosure may include at least one of the steps illustrated in FIG. 2, performed in any order. In some embodiments, a method may include at least two of the steps illustrated in FIG. 2 performed overlapping in time, or even simultaneously. Moreover, embodiments consistent with the present disclosure may include at least one but not all of the steps illustrated in FIG. 2. Furthermore, methods consistent with the present disclosure may include more steps, in addition to at least one of the steps illustrated in FIG. 2. In some embodiments, one or more steps may be repeated.

In a method 100, an inlet opening of a respiratory air measuring device is connected to a respiratory hood in step 110. In step 120, a flow generator is connected to a channel portion of the respiratory air measuring device, the channel portion including a flow nozzle oriented in a predetermined position. The flow nozzle may be positioned within the channel portion so that the generator air flow coming out of the flow nozzle in conjunction with the size and shape of the channel portion creates a measuring air flow having desired or predetermined air flow mechanics. The respiratory hood may then be positioned over or around a patient in step 130. In step 140, a component of the respiratory air of the patient in the respiratory hood is measured by a sensor device having a sensor positioned in the respiratory air measuring device as the patient's respiratory air is drawn out of the hood and flows across or through the sensor. The air flowing over or through the sensor may be a mixture of the patient's respiratory air and the room air reflowing into the hood. In step 150, the respiratory hood is removed from the patient. In step 160, the entire sensor device or just a component of the sensor device is removed to allow for easy cleaning of the respiratory air measuring device. For example, the sensor device or component of the sensor device may be removed and the rest of the respiratory air measuring device, including the flow nozzle, may be flushed with cleaning fluid or otherwise disinfected to clean the respiratory air measuring device.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A respiratory air measuring device, comprising: an inlet opening; an outlet opening, wherein a measuring air stream is configured to flow from the inlet opening to the outlet opening; a diffuser having an inlet portion and an outlet portion, wherein an inner surface of the inlet portion is coupled to an outer surface of the outlet opening, wherein the entire outlet portion extends outward from the inlet portion at a linearly sloped angle, and wherein the outlet portion is wider than the inlet portion, the diffuser configured to widen an air stream exiting the outlet opening to eliminate a negative pressure state of the exiting air stream and to output the exiting air stream directly to ambient air; a connector disposed on the inlet opening, the connector configured to fasten the respiratory air measuring device directly or indirectly to a connecting opening of a covering hood; at least one sensor device disposed adjacent to the inlet opening downstream of the connecting opening in a flow direction of the measuring air stream, the sensor device configured to measure at least one component of the respiratory air of a patient; and a flow generator disposed downstream of the sensor device in the flow direction of the measuring air stream, the flow generator configured to generate the measuring air stream in a channel portion having a free cross-section between 100 mm$^2$ and 600 mm$^2$ and that is open to the inlet opening and to the outlet opening, the flow generator comprising: an air connection configured to supply a generator air stream with an overpressure of up to 0.5 bar; and at least one flow nozzle from which the generator air stream is configured to exit, the flow nozzle configured to affect the generator air stream flow so that the generator air stream creates the measuring air stream.

2. The respiratory air measuring device of claim 1, wherein the connector is configured to be fastened to a complementary connecting opening on the covering hood.

3. The respiratory air measuring device of claim 1, wherein the connector is releasably connected to a flexible hose portion having an end remote from the connecting means comprising a hose connection configured to be fastened to a complementary connecting opening on the covering hood.

4. The respiratory air measuring device of claim 1, further comprising:
   an adjustable compressed air valve is disposed directly or indirectly on the air connection, wherein the compressed air valve is configured to be connected to an external compressed air supply.

5. The respiratory air measuring device of claim 4, wherein the compressed air valve is adjustable continuously for a variable volumetric air flow with adaptation of one of the pressure and the velocity of the generator air stream.

6. The respiratory air measuring device of claim 1, further comprising:
   an adjustable blower or fan disposed directly or indirectly on the air connection.

7. The respiratory air measuring device of claim 6, wherein the blower or the fan is adjustable in stages or continuously with adaptation of one of the pressure and the velocity of the generator air stream.

8. The respiratory air measuring device of claim 1, wherein the flow nozzle has an opening cross-section between 5 mm$^2$ and 100 mm$^2$.

9. The respiratory air measuring device of claim 1, wherein the flow nozzle has an opening cross-section between 10 mm$^2$ and 50 mm$^2$.

10. The respiratory air measuring device of claim 1, wherein the flow nozzle is round and is disposed in the center of the channel portion, the channel portion having a round cross-section, and the measuring air stream is configured to circulate around a complete circumference of the flow nozzle.

11. The respiratory air measuring device of claim 1, wherein the flow nozzle is configured as an annular gap on the periphery of the channel portion having a Coanda profiled section through which the measuring air stream is configured to flow.

12. The respiratory air measuring device of claim 1, wherein a component of the sensor device that is not in contact with the measuring air stream is removable from the respiratory air measuring device.

13. The respiratory air measuring device of claim 1, wherein the sensor device is removable from the respiratory air measuring device.

14. The respiratory air measuring device of claim 1, wherein a component of the sensor device that is in contact with the measuring air stream is configured to be replaceable as a consumable item.

15. The respiratory air measuring device of claim 1, further comprising a volumetric flow measuring device for measuring the volumetric flow of the measuring air stream disposed between the connecting opening and the flow generator.

16. The respiratory air measuring device of claim 1, wherein the respiratory air measuring device is configured to be disinfected or sterilized after one of decoupling of lines and detachment of removable components.

17. The respiratory air measuring device of claim 16, wherein the respiratory air measuring device is configured to be dismantled into individual portions for one of disinfection and sterilization.

18. A respiratory air measuring device, comprising: a housing having an inlet opening, an outlet opening, and a channel portion disposed between the inlet portion and the outlet portion, wherein a measuring air stream is configured to flow from the inlet opening to the outlet opening; a connector configured to fasten the inlet opening to a respiratory hood; at least one sensor device disposed adjacent to the inlet opening and configured to measure at least one component of respiratory air of a patient; a flow generator configured to generate the measuring air stream in the channel portion, the flow generator comprising: an air connection configured to supply a generator air stream with an overpressure of up to 0.5 bar from a generator; and a flow nozzle configured to direct the generator air stream to create the measuring air stream; and a diffuser having an inlet portion and an outlet portion, wherein an inner surface of the inlet portion is coupled to an outer surface of the outlet opening, wherein the entire outlet portion extends angularly and linearly outward from the inlet portion, and wherein the outlet portion is wider than the inlet portion, the outlet portion configured to widen an air stream exiting the outlet opening to eliminate a negative pressure state of the exiting air stream and to output the exiting air stream directly to ambient air.

19. The respiratory air measuring device of claim 18, wherein the flow nozzle comprises an annular gap on the periphery of the channel portion, the annular gap having a Coanda profiled section through which the measuring air stream is configured to flow.

20. A method of measuring respiratory air, the method comprising: connecting an inlet opening of a respiratory aft measuring device to a respiratory hood; connecting a flow generator to a channel portion of the respiratory aft measuring device, the channel portion including a flow nozzle oriented in a predetermined position; generating, by the flow generator, a generator air stream with an overpressure of up to 0.5 bar to create a measuring air flow in the respiratory air measuring device; measuring, by at least one sensor disposed adjacent to the inlet opening, at least one component of respiratory air of a patient positioned within the respiratory hood, the measuring air flow flowing from the inlet opening, past the at least one sensor and out an outlet opening; and connecting an inlet portion of a diffuser to an outer surface of the outlet opening so that an outlet portion of the diffuser widens angularly and linearly outward from the inlet portion, widening the air flow exiting the outlet opening to eliminate a negative pressure state of the exiting air stream and to output the exiting air stream directly to ambient air.

\* \* \* \* \*